(12) United States Patent
Newton

(10) Patent No.: US 10,376,407 B2
(45) Date of Patent: Aug. 13, 2019

(54) USING WICKING MATERIAL TO COLLECT URINE FROM A MALE FOR TRANSPORT

(71) Applicant: PureWick Corporation, El Cajon, CA (US)

(72) Inventor: Raymond John Newton, Bonsall, CA (US)

(73) Assignee: PUREWICK CORPORATION, Spring Valley, CA (US)

( * ) Notice: Subject to any disclaimer, the term of this patent is extended or adjusted under 35 U.S.C. 154(b) by 257 days.

(21) Appl. No.: 15/238,427

(22) Filed: Aug. 16, 2016

(65) Prior Publication Data

US 2018/0049910 A1 Feb. 22, 2018

(51) Int. Cl.
*A61F 5/453* (2006.01)
*A01K 23/00* (2006.01)

(52) U.S. Cl.
CPC ............ *A61F 5/453* (2013.01); *A01K 23/005* (2013.01)

(58) Field of Classification Search
CPC .............................. A01K 23/005; A61F 5/453
See application file for complete search history.

(56) References Cited

U.S. PATENT DOCUMENTS

| | | |
|---|---|---|
| 3,349,768 A | 10/1967 | Keane |
| 3,511,241 A | 5/1970 | Lee |
| 3,651,810 A | 3/1972 | Ormerod |
| 4,233,025 A | 11/1980 | Larson et al. |
| 4,246,901 A | 1/1981 | Frosch et al. |
| 4,453,938 A | 6/1984 | Brendling |
| 4,610,675 A | 9/1986 | Triunfol |
| 4,627,846 A | 12/1986 | Ternstroem |
| 4,631,061 A | 12/1986 | Martin |
| 4,650,477 A | 3/1987 | Johnson |

(Continued)

FOREIGN PATENT DOCUMENTS

| | | |
|---|---|---|
| DE | 102011103783 A1 | 12/2012 |
| JP | 2001054531 | 2/2001 |

(Continued)

OTHER PUBLICATIONS

Corrected International Search Report and Written Opinion for International Application No. PCT/US2017/043025 dated Jan. 11, 2018.

(Continued)

*Primary Examiner* — Tatyana Zalukaeva
*Assistant Examiner* — Gabriella E Burnette
(74) *Attorney, Agent, or Firm* — Dorsey & Whitney LLP

(57) ABSTRACT

A device for collecting urine flowing from a penis in such a manner that the urine can be transported from the device as the urine is being collected. The device includes a flexible layer of porous material; flexible wicking material disposed on one side of the layer of porous material; and a flexible layer of impermeable material secured to the periphery of the other side of the layer of porous material and so covering the other side of the layer of porous material as to define a chamber between the layer of porous material and the layer of impermeable material. Urine can be collected within the chamber for transport through a tube extending into the chamber through a port in the layer of impermeable material. The device includes a receptacle for receiving the head of a penis.

16 Claims, 1 Drawing Sheet

(56) References Cited

U.S. PATENT DOCUMENTS

| | | | |
|---|---|---|---|
| 4,747,166 A * | 5/1988 | Kuntz | A61F 5/455 4/144.1 |
| 4,772,280 A | 9/1988 | Rooyakkers | |
| 4,790,835 A | 12/1988 | Elias | |
| 4,795,449 A | 1/1989 | Schneider et al. | |
| 4,846,909 A | 7/1989 | Klug et al. | |
| 4,886,508 A | 12/1989 | Washington | |
| 4,905,692 A | 3/1990 | More | |
| 5,002,541 A | 3/1991 | Conkling et al. | |
| 5,031,248 A | 7/1991 | Kemper | |
| 5,084,037 A | 1/1992 | Barnett | |
| 5,195,997 A | 3/1993 | Carns | |
| 5,244,458 A | 9/1993 | Takasu | |
| 5,300,052 A | 4/1994 | Kubo | |
| 5,382,244 A | 1/1995 | Telang | |
| 5,636,643 A | 6/1997 | Argenta et al. | |
| 5,678,564 A | 10/1997 | Lawrence et al. | |
| 5,687,429 A | 11/1997 | Rahlff | |
| 5,695,485 A | 12/1997 | Duperret et al. | |
| 5,752,944 A | 5/1998 | Dann et al. | |
| 5,827,247 A | 10/1998 | Kay | |
| 5,827,250 A | 10/1998 | Fujioka et al. | |
| 5,827,257 A | 10/1998 | Fujioka et al. | |
| 5,894,608 A | 4/1999 | Birbara | |
| 5,911,222 A | 6/1999 | Lawrence et al. | |
| 6,063,064 A | 5/2000 | Tuckey | |
| 6,105,174 A | 8/2000 | Karlsten et al. | |
| 6,113,582 A | 9/2000 | Dwork | |
| 6,117,163 A | 9/2000 | Bierman | |
| 6,123,398 A | 9/2000 | Arai et al. | |
| 6,129,718 A | 10/2000 | Wada et al. | |
| 6,177,606 B1 | 1/2001 | Etheredge et al. | |
| 6,209,142 B1 | 4/2001 | Mattsson et al. | |
| 6,248,096 B1 | 6/2001 | Dwork et al. | |
| 6,336,919 B1 | 1/2002 | Davis et al. | |
| 6,338,729 B1 | 1/2002 | Wada et al. | |
| 6,409,712 B1 | 6/2002 | Dutari et al. | |
| 6,416,500 B1 | 7/2002 | Wada et al. | |
| 6,479,726 B1 | 11/2002 | Cole et al. | |
| 6,540,729 B1 | 4/2003 | Wada et al. | |
| 6,547,771 B2 | 4/2003 | Robertson et al. | |
| 6,592,560 B2 | 7/2003 | Snyder et al. | |
| 6,620,142 B1 | 9/2003 | Flueckiger | |
| 6,702,793 B1 | 3/2004 | Sweetser et al. | |
| 6,706,027 B2 | 3/2004 | Harvie et al. | |
| 6,740,066 B2 * | 5/2004 | Wolff | A61B 5/20 604/319 |
| 6,814,547 B2 | 11/2004 | Childers et al. | |
| 6,849,065 B2 | 2/2005 | Schmidt et al. | |
| 6,912,737 B2 | 7/2005 | Ernest et al. | |
| 6,918,899 B2 | 7/2005 | Harvie | |
| 7,018,366 B2 | 3/2006 | Easter | |
| 7,131,964 B2 | 11/2006 | Harvie | |
| 7,135,012 B2 | 11/2006 | Harvie | |
| 7,141,043 B2 | 11/2006 | Harvie | |
| 7,171,699 B2 | 2/2007 | Ernest et al. | |
| 7,181,781 B1 | 2/2007 | Trabold et al. | |
| 7,192,424 B2 | 3/2007 | Cooper | |
| 7,220,250 B2 * | 5/2007 | Suzuki | A61F 5/451 604/317 |
| 7,335,189 B2 | 2/2008 | Harvie | |
| 7,699,831 B2 | 4/2010 | Bengtson et al. | |
| 7,866,942 B2 | 1/2011 | Harvie | |
| 7,871,385 B2 | 1/2011 | Levinson et al. | |
| 7,875,010 B2 | 1/2011 | Frazier et al. | |
| 7,901,389 B2 | 3/2011 | Mombrinie | |
| 7,927,321 B2 | 4/2011 | Marland | |
| 7,931,634 B2 | 4/2011 | Swiecicki et al. | |
| 7,993,318 B2 | 8/2011 | Olsson et al. | |
| 8,181,651 B2 | 5/2012 | Pinel | |
| 8,211,063 B2 | 7/2012 | Bierman et al. | |
| 8,241,262 B2 | 8/2012 | Mahnensmith | |
| 8,277,426 B2 | 10/2012 | Wilcox et al. | |
| 8,287,508 B1 * | 10/2012 | Sanchez | A61F 5/4404 604/317 |
| 8,425,482 B2 | 4/2013 | Khoubnazar | |
| 8,551,075 B2 | 10/2013 | Bengtson | |
| 8,568,376 B2 | 10/2013 | Delattre et al. | |
| 8,585,683 B2 | 11/2013 | Bengtson et al. | |
| 8,715,267 B2 | 5/2014 | Bengtson et al. | |
| 8,864,730 B2 | 10/2014 | Conway et al. | |
| 8,936,585 B2 | 1/2015 | Carson et al. | |
| 9,248,058 B2 | 2/2016 | Conway et al. | |
| 9,480,595 B2 | 11/2016 | Baham et al. | |
| 2002/0026161 A1 | 2/2002 | Grundke | |
| 2003/0195484 A1 | 10/2003 | Harvie | |
| 2004/0127872 A1 | 7/2004 | Petryk et al. | |
| 2004/0236292 A1 | 11/2004 | Tazoe et al. | |
| 2004/0254547 A1 | 12/2004 | Okabe et al. | |
| 2005/0070862 A1 | 3/2005 | Tazoe et al. | |
| 2005/0097662 A1 | 5/2005 | Leimkuhler et al. | |
| 2005/0101924 A1 | 5/2005 | Elson et al. | |
| 2005/0177070 A1 | 8/2005 | Levinson et al. | |
| 2005/0279359 A1 | 12/2005 | LeBlanc et al. | |
| 2006/0200102 A1 | 9/2006 | Cooper | |
| 2006/0229576 A1 | 10/2006 | Conway et al. | |
| 2006/0235359 A1 | 10/2006 | Marland | |
| 2007/0006368 A1 | 1/2007 | Key et al. | |
| 2008/0234642 A1 | 9/2008 | Patterson et al. | |
| 2008/0287894 A1 | 11/2008 | Van Den Heuvel et al. | |
| 2009/0025717 A1 | 1/2009 | Pinel | |
| 2009/0056003 A1 | 3/2009 | Ivie et al. | |
| 2009/0281510 A1 | 11/2009 | Fisher | |
| 2010/0185168 A1 | 7/2010 | Graauw et al. | |
| 2010/0263113 A1 | 10/2010 | Shelton et al. | |
| 2011/0034889 A1 | 2/2011 | Smith | |
| 2011/0040271 A1 | 2/2011 | Rogers et al. | |
| 2011/0054426 A1 | 3/2011 | Stewart et al. | |
| 2011/0202024 A1 | 8/2011 | Cozzens | |
| 2012/0103347 A1 | 5/2012 | Wheaton et al. | |
| 2012/0165768 A1 | 6/2012 | Sekiyama et al. | |
| 2012/0245547 A1 | 9/2012 | Wilcox et al. | |
| 2012/0330256 A1 | 12/2012 | Wilcox et al. | |
| 2013/0053804 A1 | 2/2013 | Soerensen et al. | |
| 2014/0031774 A1 | 1/2014 | Bengtson | |
| 2014/0196189 A1 | 7/2014 | Lee et al. | |
| 2015/0047114 A1 | 2/2015 | Ramirez | |
| 2015/0209194 A1 | 7/2015 | Heyman | |
| 2015/0366699 A1 | 12/2015 | Nelson | |
| 2016/0100976 A1 | 4/2016 | Conway et al. | |
| 2016/0367226 A1 | 12/2016 | Newton et al. | |
| 2016/0367411 A1 | 12/2016 | Justiz et al. | |
| 2016/0374848 A1 | 12/2016 | Sanchez et al. | |
| 2017/0143534 A1 | 5/2017 | Sanchez | |
| 2017/0189225 A1 | 7/2017 | Voorhees et al. | |
| 2017/0042748 A1 | 12/2017 | Griffin | |
| 2018/0228642 A1 | 8/2018 | Davis et al. | |

FOREIGN PATENT DOCUMENTS

| | | |
|---|---|---|
| WO | 9309736 A2 | 5/1993 |
| WO | 2008078117 A1 | 7/2008 |

OTHER PUBLICATIONS

International Search Report and Written Opinion for International Application No. PCT/US2017/043025 dated Oct. 18, 2017.

"Male Urinary Pouch External Collection Device", http://www.hollister.com/en/products/Continence-Care-Products/Urine-Collectors/Urine-Collection-Accessories/Male-Urinary-Pouch-External-Collection-Device, last accessed Feb. 8, 2018.

"Step by Step How Ur24 WorksHome", http://medicalpatentur24.com, last accessed Dec. 6, 2017, Aug. 30, 2017, 4 pages.

Advisory Action for U.S. Appl. No. 14/952,591 dated Jun. 1, 2018.

AMXDmax In-Flight Bladder Relief; Omni Medical 2015; Omni Medical Systems, Inc.

Final Office Action for U.S. Appl. No. 14/952,591 dated Feb. 23, 2018.

Final Office Action for U.S. Appl. No. 14/947,759, dated Apr. 8, 2016 (8 pages).

International Search Report and Written Opinion for International Patent Application No. PCT/US16/49274, dated Dec. 1, 2016 (11 pages).

(56) References Cited

OTHER PUBLICATIONS

International Search Report and Written Opinion of the International Searching Authority for International Patent Application No. PCT/US2017/035625, dated Aug. 15, 2017 (17 pages).
Non-Final Office Action for U.S. Appl. No. 14/952,591 dated Aug. 1, 2017.
Non-Final Office Action for U.S. Appl. No. 14/952,591 dated Sep. 28, 2018.
Non-Final Office Action for U.S. Appl. No. 15/171,968 dated Jun. 2018.
Non-Final Office Action for U.S. Appl. No. 15/221,106 dated Jun. 5, 2018.
Non-Final Office Action for U.S. Appl. No. 15/260,103 dated Sep. 26, 2018.
Non-Final Office Action for U.S. Appl. No. 15/611,587 dated Jul. 13, 2018.
Non-Final Office Action for U.S. Appl. No. 15/611,587 dated Dec. 29, 2017.
Non-Final Office Action for U.S. Appl. No. 14/947,759, dated Mar. 17, 2016.
U.S. Appl. No. 15/260,103, filed Sep. 8, 2016.
U.S. Appl. No. 15/611,587, filed Jun. 1, 2017.
U.S. Appl. No. 15/612,325, filed Jun. 2, 2017.
U.S. Appl. No. 62/665,297, filed May 1, 2018.
U.S. Appl. No. 62/665,302, filed May 1, 2018.
U.S. Appl. No. 62/665,317, filed May 1, 2018.
U.S. Appl. No. 62/665,321, filed May 1, 2018.
U.S. Appl. No. 62/665,331, filed May 1, 2018.
U.S. Appl. No. 62/665,335, filed May 1, 2018.
U.S. Appl. No. 15/171,968, filed Jun. 2, 2016.
Parmar, "10 Finalists Chosen for Dare-to-Dream Medtech Design Challenge (PUreWick)," Design Services, Nov. 10, 2014 (3 pages).
Purewick, "Incontinence Relief for Women" Presentation, (7 pages), Sep. 23, 2015.
Pytlik, "Super Absorbent Polymers," University of Buffalo http://www.courses.sens.buffalo.edu/ce435/Diapers/Diapers.html, accessed on Feb. 17, 2017.
Final Office Action for U.S. Appl. No. 15/171,968 dated Mar. 19, 2019.
Final Office Action for U.S. Appl. No. 15/221,106 dated Jan. 23, 2019.
Final Office Action for U.S. Appl. No. 15/260,103 dated Feb. 14, 2019.
Issue Notification for U.S. Appl. No. 15/611,587 dated Feb. 20, 2019.
Non-Final Office Action for U.S. Appl. No. 14/952,591 dated Mar. 21, 2019.
Notice of Allowance for U.S. Appl. No. 15/611,587 dated Dec. 21, 2018.
U.S. Appl. No. 16/369,676, filed Mar. 29, 2019.
Notice of Allowance for U.S. Appl. No. 15/221,106 dated May 1, 2019.
Notice of Allowance for U.S. Appl. No. 15/260,103 dated Jun. 7, 2019.
U.S. Appl. No. 16/449,039, filed Jun. 21, 2019.

* cited by examiner

USING WICKING MATERIAL TO COLLECT URINE FROM A MALE FOR TRANSPORT

BACKGROUND OF THE INVENTION

The invention generally pertains to using wicking material to collect urine for transport and is particularly directed to a device that can be used to so collect urine from the penis of a person or an animal in such a manner that the urine can be readily transported from the device as the urine is being collected.

A container for collecting urine and transporting the collected urine voided from a person's body is described in U.S. Pat. No. 8,287,508 to Robert A. Sanchez. The container described in said patent is made of plastic or some other material and defines a chamber for collecting urine. The container is closed, except for having an array of openings through which urine can be drawn into the chamber for collection and at least one port through which urine can be drawn away from the chamber by a transport tube inserted into the chamber. The exterior of the container is configured for enabling a moisture-wicking article to be secured over the array of openings and for enabling the secured moisture-wicking article to be disposed in contact with the region of a female body surrounding the urethral opening. A vacuum pump is attached to the transport tube in order to create a partial vacuum in the chamber in order to draw urine into the chamber for collection of the urine and in order to draw the collected urine away from the chamber.

A device that can be used to so collect urine from the urethra of a woman in such a manner that the urine can be readily transported from the device as the urine is being collected is described in U.S. Pat. No. 4,747,166 to David H. Kuntz.

SUMMARY OF THE INVENTION

The invention provides a device that can be used to so collect urine flowing from the penis of a person or an animal in such a manner that the urine can be transported from the device as the urine is being collected, the device comprising: a flexible layer of porous material; flexible wicking material disposed on one side of the layer of porous material; and a flexible layer of impermeable material secured to the periphery of the other side of the layer of porous material and so covering the other side of the layer of porous material as to define a chamber between the layer of porous material and the layer of impermeable material, within which chamber urine can be collected for transport, with the chamber having a port for receiving a tube so that urine collected within the chamber can be transported from the chamber by being drawn from the chamber when a partial vacuum is applied within the chamber via a said received tube; wherein the combination of the wicking material, the layer of porous material and the layer of impermeable material is so dimensioned and configured as to provide a receptacle for receiving the head of a penis, from which receptacle urine flowing from said penis can be drawn through the wicking material and the porous material into the chamber when a said partial vacuum is applied within the chamber via said received tube.

The invention is particularly useful for persons or animals during various circumstances. These circumstances include a condition such as incontinence or a disability that limits or impairs mobility. These circumstances also include restricted travel conditions, such as sometimes experienced by pilots, drivers, workers in hazardous areas, etc. These circumstances further include collection of urine for monitoring purposes or clinical testing.

Additional features of the invention are described with reference to the detailed description.

DETAILED DESCRIPTION

Figure 1:
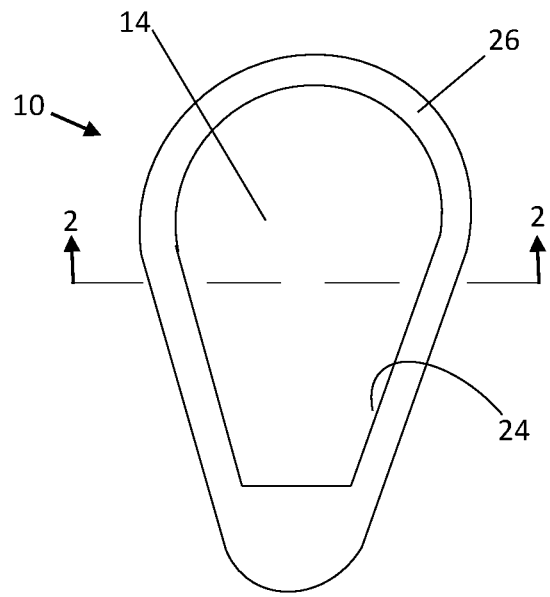
FIG. 1 is a top view of an exemplary embodiment of a urine collection device according to the invention.
Figure 2:
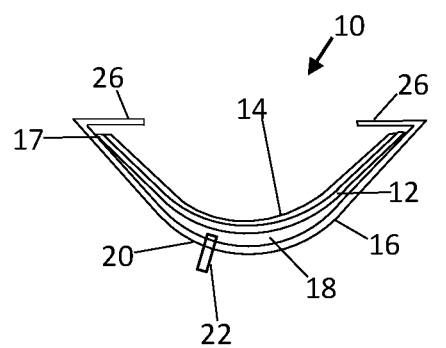
FIG. 2 is a (non-cross-hatched) sectional view taken along line 2-2 in FIG. 1 showing various components included in the urine collection device shown in FIG. 1.

Referring to FIGS. 1 and 2, an exemplary embodiment of a urine collection device 10 according to the invention includes a flexible layer of porous material 12; flexible wicking material 14 disposed on one side of the layer of porous material 12; and a flexible layer of impermeable material 16 secured to the periphery 17 of the other side of the layer of porous material 12. The layer of impermeable material 16 so covers the other side of the layer of porous material 12 as to define a chamber 18 between the layer of porous material 12 and the layer of impermeable material 16. Urine can be collected within the chamber 18 for transport. The chamber 18 has a port 20 for receiving a tube 22 so that urine collected within the chamber 18 can be transported from the chamber 18 by being drawn from the chamber 18 when a partial vacuum is applied within the chamber 18 via the received tube 22. The received tube 22 extends past the port 20 to within the chamber 18.

The combination of the wicking material 14, the layer of porous material 12 and the layer of impermeable material 16 is so dimensioned and configured as to provide a receptacle 24 for receiving the head of a penis. Urine flowing from the penis can be drawn from the receptacle 24 through the wicking material 14 and the porous material 12 into the chamber 18 when a partial vacuum is applied within the chamber 18 via the received tube 22.

The layer of impermeable material 16 extends beyond covering the other side of the layer of porous material 12 and thence inward over the receptacle 24 to thereby provide a lip 26 for retaining urine within the receptacle 24.

In the exemplary embodiment, the wicking material 14 is medical gauze. In other embodiments, other wicking materials are used for the wicking material.

In the exemplary embodiment, the porous material 12 is provided as a web of a spun plastic material, such as nylon or polyester. In other embodiments, other materials are used as the porous material.

The exemplary embodiment, FIG. 1 shows a receptacle 24 that has an irregular shape. In other embodiments, the shape may be generally oblong, oval or round.

In FIGS. 1 and 2, the relative dimensions of the various components are not shown to scale.

Different embodiments of a male urine collection device according to the invention are dimensioned and configured for use in both adult and pediatric applications, and for veterinary applications involving animals of different species and sizes.

When a man is lying on his back with the head of his penis disposed within the receptacle 24 and a partial vacuum is applied within the chamber 18 via the received tube 22, urine flowing from the penis runs down the inner sides of the receptacle 24 and from the receptacle 24 through the wicking material 14 and the porous material 12 into the chamber 18 and thence to the received tube 22, through which the urine is transported from the chamber 18. The urine collection device 10 can thus advantageously capture and transport urine as it flows against gravity without having to attach a catheter to the penis.

The benefits specifically stated herein do not necessarily apply to every conceivable embodiment of the present invention. Further, such stated benefits of the present invention are only examples and should not be construed as the only benefits of the present invention.

While the above description contains much specificity, these specifics are not to be construed as limitations on the scope of the present invention, but rather as examples of the embodiments described herein. Other variations are possible and the scope of the present invention should be determined not by the embodiments described herein but rather by the claims and their legal equivalents.

The invention claimed is:

1. A device for use to collect urine flowing from a penis of a person or an animal in such a manner that the urine can be transported from the device as the urine is being collected, the device comprising:
   a flexible layer of porous material having a first side and a second side;
   flexible wicking material having a first side and a second side, the second side of the flexible wicking material being disposed on the first side of the flexible layer of porous material;
   a flexible layer of impermeable material defining an interior portion of the device, the flexible layer of porous material and the flexible wicking material being positioned within the interior portion defined by the flexible layer of impermeable material with at least a portion of the second side of the flexible layer of porous material secured to the flexible layer of impermeable material;
   a chamber of void space positioned within the interior portion of the device between the flexible layer of porous material and the flexible layer of impermeable material, the chamber being defined at least partially by the second side of the porous material and the flexible layer of impermeable material and configured to collect urine for transport, the chamber having a port for receiving a tube to transport urine from the chamber by drawing urine from the chamber through the tube when a vacuum is applied within the chamber via the tube received by the port; and
   a receptacle within the interior portion of the device dimensioned and configured to receive a head of the penis within the receptacle, the receptacle being defined at least partially by at least a portion of the first side of the flexible wicking material, wherein the flexible wicking material and the flexible layer of impermeable material are dimensioned and configured to shape the receptacle to receive the head of the penis therein, wherein the receptacle is configured to draw urine flowing from said penis through the flexible wicking material and the porous material into the chamber when the head of the penis is disposed within the receptacle and the vacuum is applied within the chamber via the tube received by the port.

2. The device according to claim 1, wherein the flexible layer of impermeable material extends beyond covering the other side of the flexible layer of porous material and hence inward over the receptacle to thereby provide a lip for retaining urine within the receptacle.

3. The device according to claim 2, wherein the lip of the flexible layer of impermeable material defines a receptacle opening of the receptacle.

4. The device according to claim 3, wherein the port is positioned opposite to the receptacle opening.

5. The device according to claim 1, wherein the flexible wicking material includes gauze.

6. The device according to claim 1, wherein the flexible layer of porous material includes a web of a spun plastic material, the spun plastic material including at least one of nylon or polyester.

7. A urine collection device, comprising:
   an impermeable material defining an interior portion of the urine collection device;
   an opening in the impermeable material;
   wicking material positioned within the interior portion of the urine collection device;
   a flexible porous material positioned at least partially between the wicking material and at least a portion of the impermeable material;
   a chamber positioned substantially opposite to the opening, the chamber being partially defined by a portion of the flexible porous material and a portion of the impermeable material;
   a port extending through the impermeable material to the chamber, the port being positioned substantially opposite to the opening of the cavity and configured to receive a tube to transport urine from the chamber through the tube.

8. The urine collection device of claim 7, further comprising a receptacle defined at least partially by the wicking material, the receptacle extending from the opening into the interior portion of the urine collection device and being shaped to receive at least a head of a penis, wherein the receptacle is configured to draw urine flowing from the head of the penis through the wicking material and the flexible porous material into the chamber when the head of the penis is disposed within the receptacle and a vacuum is applied within the chamber via the tube received by the port.

9. The urine collection device of claim 7, wherein the chamber is void space positioned between the portion of the flexible porous material and the the portion of the impermeable material defining the chamber.

10. The urine collection device of claim 7, wherein a portion of the wicking material is positioned opposite to the opening and adjacent to the portion of the flexible porous material defining the chamber.

11. The urine collection device of claim 7, further comprising a lip defining the opening, the lip including impermeable material.

12. The urine collection device of claim 7, wherein the porous material includes a web of spun material.

13. A urine collection device, comprising:
   impermeable material defining an interior portion of the urine collection device;
   wicking material positioned within the interior portion;
   porous material positioned within the interior portion, at least a portion of the porous material being positioned between the layer of impermeable material and the wicking material;
   a receptacle defined at least partially by the wicking material and shaped to receive at least a head of a penis, the receptacle having an opening and extending from the opening into interior portion of the urine collection device; and
   a chamber of void space positioned substantially opposite to the opening of the receptacle, the chamber being defined by a portion of the porous material and a portion of the impermeable material, wherein the wicking material and the impermeable material are dimensioned to shape the receptacle to draw urine flowing from the head of the penis through the wicking material and the porous material into the chamber when the head of the penis is disposed within the receptacle.

14. The urine collection device of claim 13, further comprising a port extending through the portion of the impermeable material to the chamber, the port being positioned substantially opposite to the opening of the cavity and configured to receive a tube to transport urine from the chamber through the tube, wherein the receptacle is configured to draw urine flowing from the head of the penis through the wicking material and the porous material into the chamber when a vacuum is applied within the chamber via the tube received by the port.

15. The urine collection device of claim 13, wherein a portion of the wicking material is positioned opposite to the opening of the receptacle and adjacent to the portion of the porous material defining the chamber.

16. The urine collection device of claim 13, further comprising a lip defining the opening of the receptacle, the lip including impermeable material.

* * * * *